(12) United States Patent
Sauter-Starace et al.

(10) Patent No.: US 8,075,754 B2
(45) Date of Patent: Dec. 13, 2011

(54) ELECTROWETTING PUMPING DEVICE AND USE FOR MEASURING ELECTRICAL ACTIVITY

(75) Inventors: Fabien Sauter-Starace, Seyssinet-Pariset (FR); Jean Berthier, Meylan (FR)

(73) Assignee: Commissariat a l'Energie Atomique, Paris (FR)

( * ) Notice: Subject to any disclaimer, the term of this patent is extended or adjusted under 35 U.S.C. 154(b) by 922 days.

(21) Appl. No.: 11/917,857

(22) PCT Filed: Jun. 16, 2006

(86) PCT No.: PCT/FR2006/050566
§ 371 (c)(1),
(2), (4) Date: Dec. 17, 2007

(87) PCT Pub. No.: WO2006/134307
PCT Pub. Date: Dec. 21, 2006

(65) Prior Publication Data
US 2008/0210558 A1    Sep. 4, 2008

(30) Foreign Application Priority Data

Jun. 17, 2005 (FR) ..................... 05 51662

(51) Int. Cl.
*G01N 27/26* (2006.01)
(52) U.S. Cl. ...................... 204/450; 204/600
(58) Field of Classification Search .................. 204/450, 204/600
See application file for complete search history.

(56) References Cited

U.S. PATENT DOCUMENTS

| | | | |
|---|---|---|---|
| 6,773,566 B2 | 8/2004 | Shenderov | |
| 7,052,244 B2 | 5/2006 | Fouillet et al. | |
| 2002/0063067 A1 * | 5/2002 | Bech et al. | 205/775 |
| 2004/0055536 A1 * | 3/2004 | Kolar et al. | 118/626 |
| 2005/0179746 A1 | 8/2005 | Roux et al. | |
| 2006/0163063 A1 * | 7/2006 | Picollet-Dahan et al. | 204/403.06 |

FOREIGN PATENT DOCUMENTS

| | | |
|---|---|---|
| EP | 1 386 657 A1 | 2/2004 |
| FR | 2 841 063 A1 | 12/2003 |
| WO | WO 02/07503 A1 | 1/2002 |
| WO | WO 2004/029608 A1 | 4/2004 |
| WO | WO 2004/038409 A2 | 5/2004 |

OTHER PUBLICATIONS

U.S. Appl. No. 11/631,389, filed Dec. 29, 2006, Marchand, et al.
U.S. Appl. No. 11/630,993, filed Dec. 28, 2006, Boutet.
U.S. Appl. No. 11/630,999, filed Dec. 28, 2006, Fouillet.
U.S. Appl. No. 11/722,637, filed Jun. 22, 2007, Fouillet, et al.

(Continued)

*Primary Examiner* — Jeffrey T Barton
*Assistant Examiner* — Jennifer Dieterle
(74) *Attorney, Agent, or Firm* — Oblon, Spivak, McClelland, Maier & Neustadt. L.L.P.

(57) ABSTRACT

The invention relates to a method for pumping through an orifice (30, 31) of a first substrate (1), a first volume of liquid (2) in contact with a first hydrophobic surface of said substrate, wherein a pressure variation between the first volume of liquid and a second volume of liquid (2'), located in contact with said orifice and a second hydrophobic surface of said substrate, is achieved by electrowetting.

17 Claims, 9 Drawing Sheets

OTHER PUBLICATIONS

U.S. Appl. No. 11/916,751 filed Dec. 6, 2007, Sauter-Starace, et al.

Kari T. Hjelt, et al., "High-Resolution Liquid Volume Detection in Sub-Nanoliter Reactors", Sensors and Actuators, vol. 83, 2000, pp. 61-66.

Hong Ren, et al., "Design and Testing of an Interpolating Mixing Architecture for Electrowetting-Based Droplet-On-Chip Chemical Dilution", Transducers, Solid-State Sensors, Actuators and Microsystems, $12^{th}$ International Conference on 2003, vol. 1, Jun. 8-12, 2003, 4 Pages.

Erwin Neher, et al., "Single Channel Currents Recorded from Membrane of Denervated Frog Muscle Fibres", Nature vol. 260, Apr. 29, 1976 pp. 799-802.

* cited by examiner

ELECTROWETTING PUMPING DEVICE AND USE FOR MEASURING ELECTRICAL ACTIVITY

TECHNICAL FIELD AND PRIOR ART

The invention first relates to the field of pumping and displacing microvolumes of liquid, such as microdrops.

The displacement of fluids in microfluidic systems requires the use of pumping devices which may be based on different physical principles.

At this scale, capillary forces are much larger than gravity. Several physical principles have been developed in order to displace fluids or to pressurize them.

Two families of principles are distinguished: those using mobile parts for setting fluids into motion by hydrostatic pressure or fluid-structure interaction (peristaltic pump) and those which do not use mobile parts but physical forces directly applied to the fluids.

Among the principles included in this second class, mention may be made of: electro-osmosis and thermocapillarity.

Electro-osmosis requires very high voltages in order to attain pressures of several bars. The electric fields are of the order of 200 to 1,000 V/cm. Heating by the Joule effect is inherent to this electric field, whence a heat control constraint or even an incompatibility with survival conditions of fragile chemical or biological materials.

This heating would be particularly critical in the case of resistivity measurements of the planar patch-clamp>> type. Conductivities of saline solutions are of the order of 0.5 to 4 S/m. Moreover, significant electric fields (of the order of magnitude of 200 to 8,000 V/cm for mice lung cells) would generate electroporation, i.e. permeability of the cell membrane.

The present invention also relates to a method and device for measuring electric activity of one or more biological cells and notably to a measuring device of the patch clamp>> type.

In order to study the electric activities of cells, the <<patch-clamp>> technique was proposed by Sakmann and Neher in 1976. But, recently, alternatives were sought in order to increase the success rate of this measurement and increase the number of accessible data.

Document WO04/038409 describes a device for conducting such measurements. This device is of the planar type in silicon.

Figure 14:
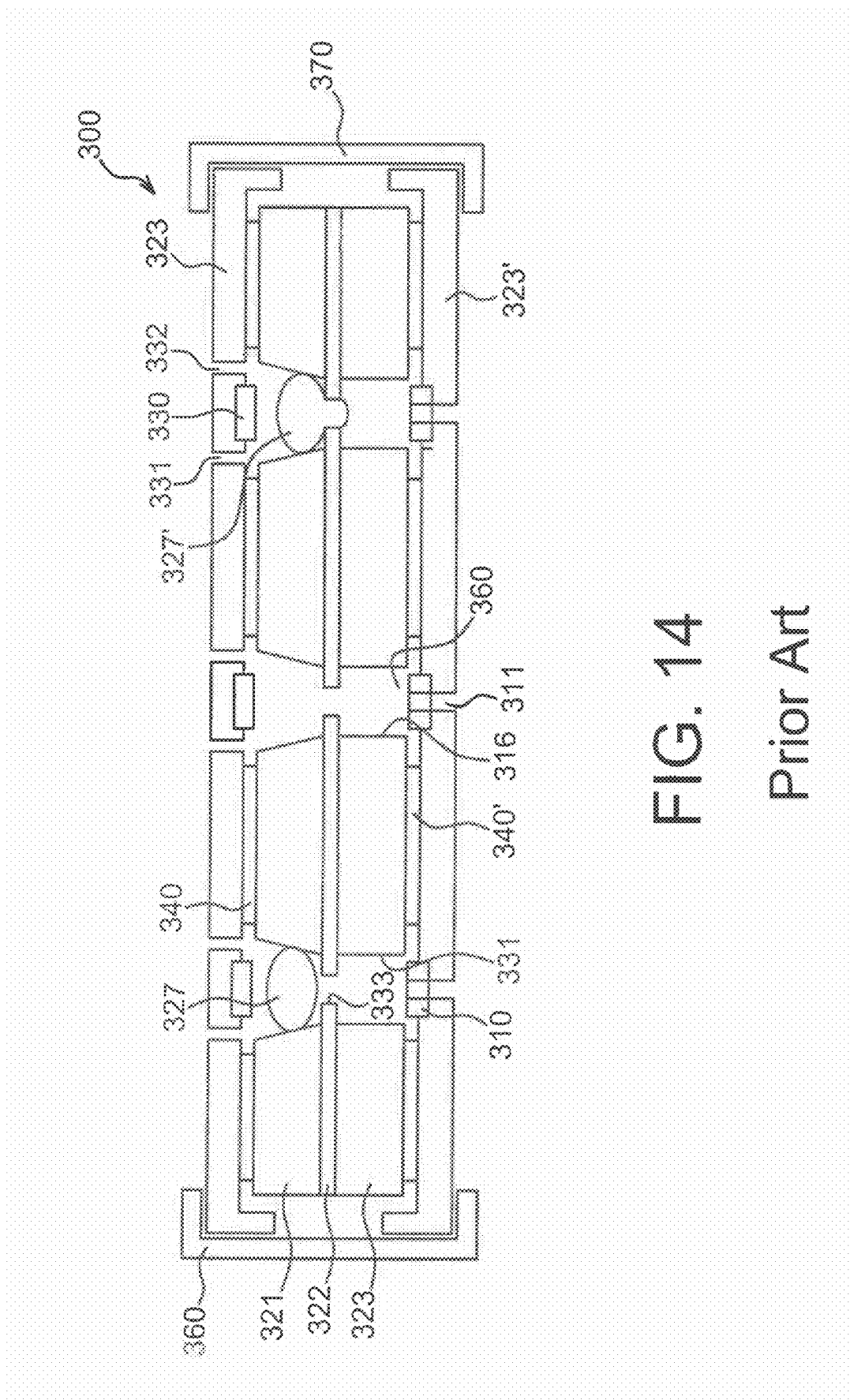

FIG. 14 illustrates a measuring device 300 of the planar patch-clamp>> type as described in document WO 2004/038409A2.

Both printed circuits 323, 323' provide the confinement of fluids in chambers 326, 326' made in wafers 321, 323, for example in silicon. These chambers are filled with an electrophysiological solution. Both of these circuits are provided with electrodes 310, 330. Gaskets 340, 340' provide the seal of the system.

An intermediate layer 322 includes an orifice 333 providing communication between the upper 326 and lower 326' chambers and allowing a cell 327 to be captured by suction. The aperture 331 of the layer 323 is of a larger size than the aperture 333.

The chip made according to this document applies a system of conduits 311, 331, 332 allowing suction of fluids. More specifically, this device includes channels intended to be connected to capillaries themselves connected to liquid suction means located outside the chip. The system is therefore complex, not compact.

Moreover, the sucked volumes are controllable with difficulty and are significant, of the order of a few tens of nanoliters to several microliters.

Jaws 360, 370 allow the whole of the system to be held.

In this type of device, the fluid volumes are conditioned by the cavities 326, 326', and by the gaskets providing the seal of the lower and upper chambers. It is therefore necessary to fill each measurement site individually, sequentially or in parallel, with a solution adapted for measuring electrical activity of ionic channels and including a cell suspension. The volume of fluid, there again, is significant and miniaturization is limited by the standards for dispensing equipment. This constraint also limits the possibilities of integration because each site should be accessible to macroscopic dispensing means.

In this type of device, management of the depressions required for capturing a single cell and for the invagination of its plasma or cell membrane is therefore achieved by means of a macroscopic system comprising two pressure generators with which a controlled pressure difference may be obtained between the upper and lower chambers.

This control of the fluids may also be obtained by pumps or push syringes.

These systems are macroscopic and their degree of parallelization remains low. They are neither both parallelizable and addressable in an independent way for each site.

These systems are macroscopic and are not compatible with the increase in the number of measurement sites, even though allowed by lithographic and collective etching methods of microtechnologies.

First, the problem is therefore posed of finding a new microfluidic pumping device, in particular which may be compatible with a device of the planar <<patch clamp>> type.

The problem is also posed of finding a new microfluidic pumping device which does not have one or more of the limitations discussed above.

DISCUSSION OF THE INVENTION

First, the invention relates to a method for pumping through an orifice of a first substrate, a first volume of liquid, in contact with a first hydrophobic surface of said substrate, wherein the pressure variation between the first liquid volume and a second liquid volume located in contact with said orifice and a second hydrophobic surface of said substrate, is achieved by electrowetting.

The first and/or the second volume of liquid may be confined at least during pumping, between said first hydrophobic surface and/or said second hydrophobic surface and a second and/or third substrate.

Such a method may apply an electrowetting device, including said first substrate, the first surface of which is hydrophobic or covered with a hydrophobic layer, and a plurality of electrodes positioned under said hydrophobic layer, pumping being achieved by activating these electrodes.

The second surface of the electrowetting device may include a hydrophobic layer and a plurality of electrodes positioned under said hydrophobic layer.

The first and second surfaces of the substrate may be parallel to each other and to a plane defined by the substrate, or else the first surface of the substrate may be parallel to a plane defined by the substrate, the second surface being then defined by at least one portion of the wall of said orifice.

The first and/or the second volume of liquid may consist of a drop of liquid, the drop(s) being for example formed from one or more reservoirs, and may for example have a volume between 1 nl and 10 µl.

The invention also relates to a method for analyzing a liquid from a first volume of liquid including:
- contacting this first volume of liquid with a hydrophobic surface,
- pumping this first volume of liquid by means of a second volume of liquid, according to a method as described above, in order to position it against said orifice,
- measuring electric activity of said liquid.

The electric activity measurement may be conducted on a single cell contained in the first volume of liquid, the measurement being for example a measurement on one cell ionic channel or on channel(s) of a cell membrane.

It may also be conducted on a biological object such as an embryo or a bovine ovocyte.

The invention also relates to a device for pumping volumes of liquid, including:
- a substrate, having a first and a second surface, at least one of which is hydrophobic, or covered with a hydrophobic layer, and at least one orifice crossing through said substrate,
- means for displacing by electrowetting, at least one volume of liquid on one of said faces of the substrate.

Said orifice may include a first portion having a first maximum dimension, and a second portion having a second maximum dimension larger than the first.

The means for displacing drops by electrowetting may include a plurality of electrodes positioned under said hydrophobic layer or surface.

The second surface of the electrowetting device may be hydrophobic or include a hydrophobic layer, a plurality of electrodes may be positioned under said hydrophobic layer or surface.

The first and second surfaces of the substrate may be parallel to each other and to a plane defined by the substrate, or even the first surface of the substrate may be parallel to a plane defined by the substrate, the second surface being defined by at least one portion of the wall of said orifice.

A device according to the invention may further include a first dielectric layer in part under the first hydrophobic layer or surface, a second dielectric layer may further be positioned on a surface parallel to the first surface.

A second substrate and/or a third substrate may be positioned facing the first and/or the second hydrophobic surface.

The second and/or the third substrate may further include a hydrophobic surface layer as well as a counter-electrode.

The invention also relates to a device for analyzing a first volume of liquid, including at least one device as above, and means for measuring the electrical activity of a volume of liquid associated with at least one orifice.

The means for measuring the electric activity may be associated with at least one orifice including first and second electrodes.

A device according to the invention may further include at least one reservoir of liquid and means, for example means for displacing drops by electrowetting, for bringing drops of liquid from this reservoir or from at least one of these reservoirs towards one of the orifices.

SHORT DESCRIPTION OF THE DRAWINGS

Figure 1A:
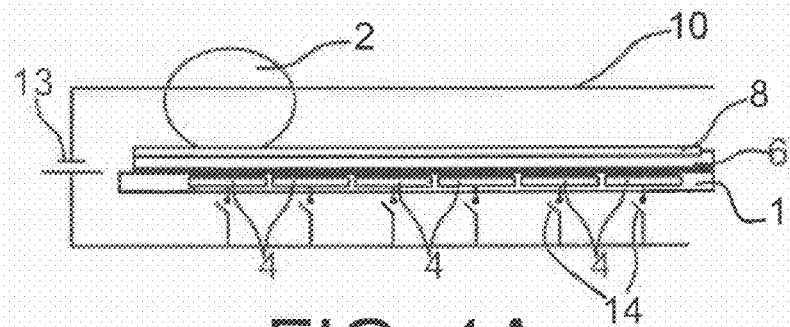
Figure 1B:
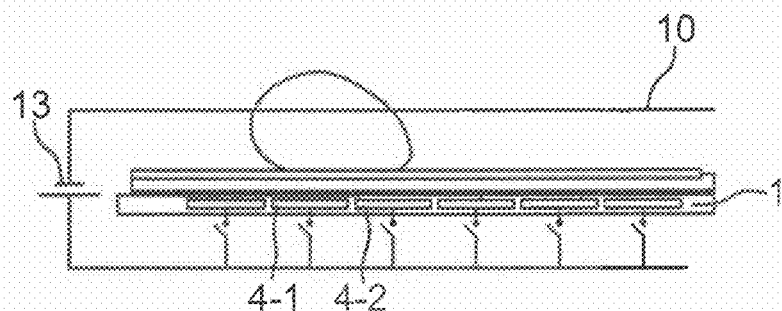
Figure 1C:
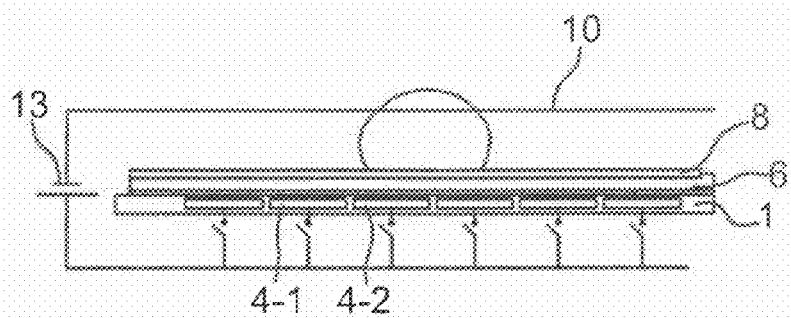
Figure 2:
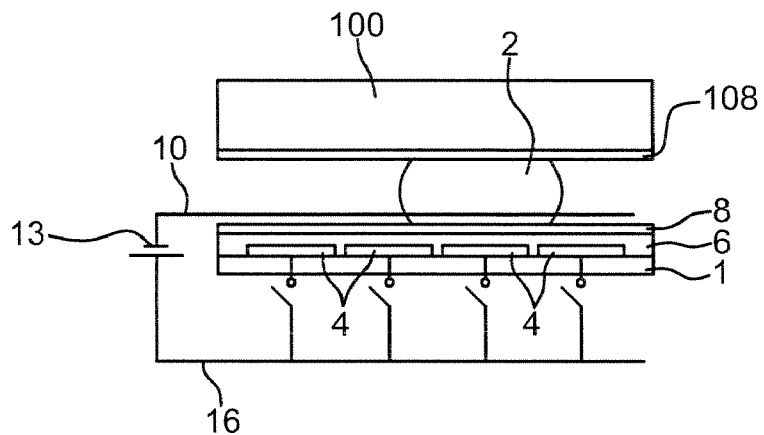
Figure 3A:
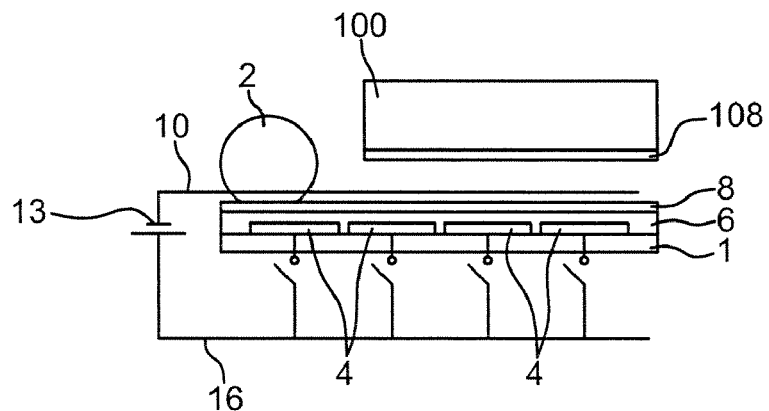
Figure 3B:
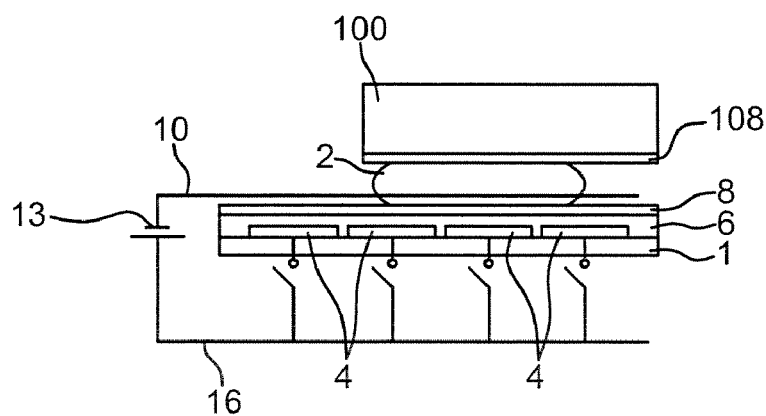
Figure 4:
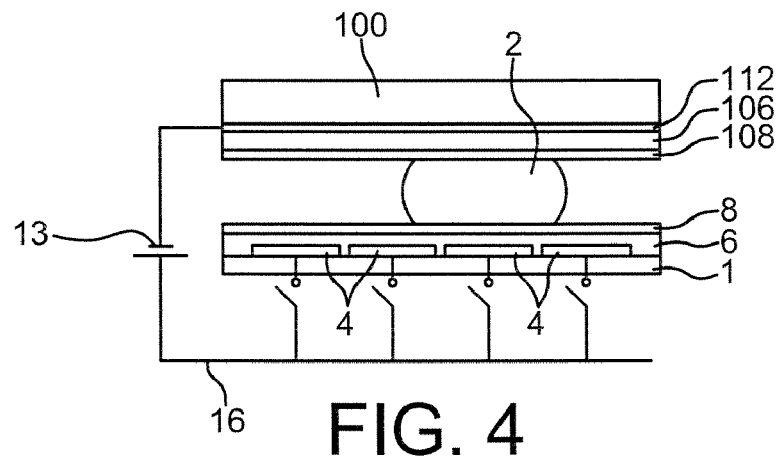
Figure 5A:
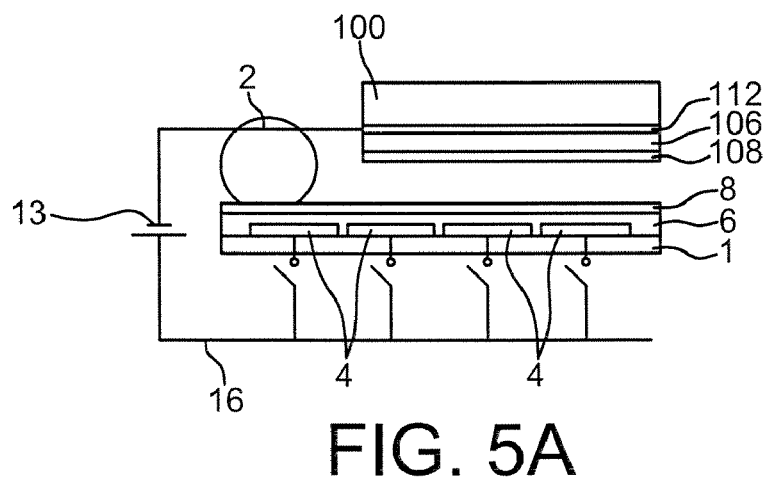
Figure 5B:
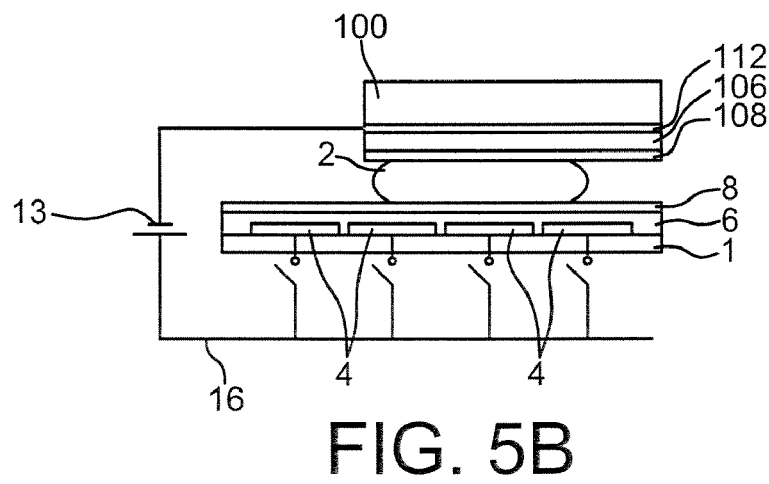
Figure 6A:
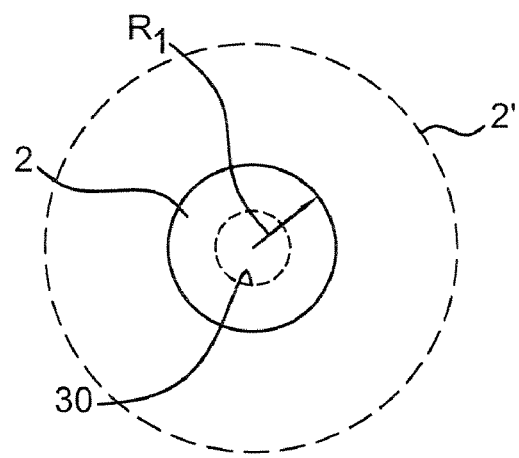
Figure 6B:
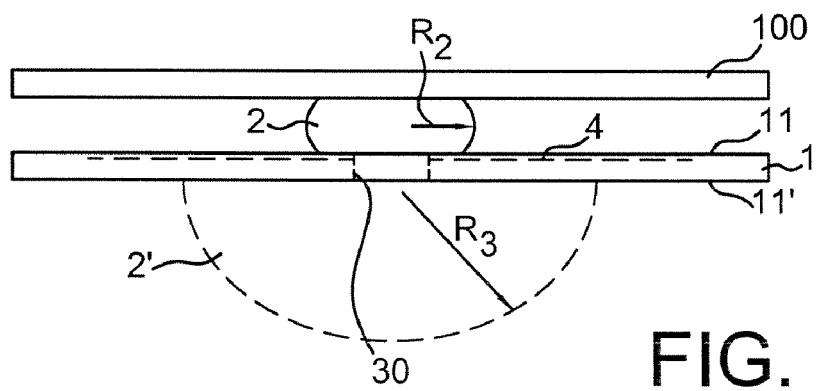
Figure 7A:
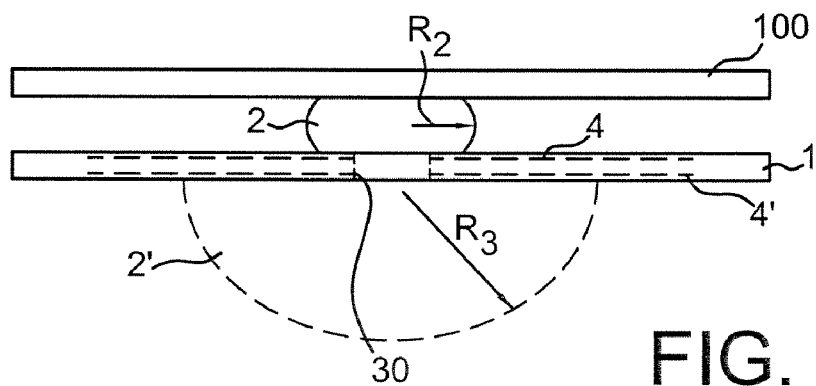
Figure 7B:
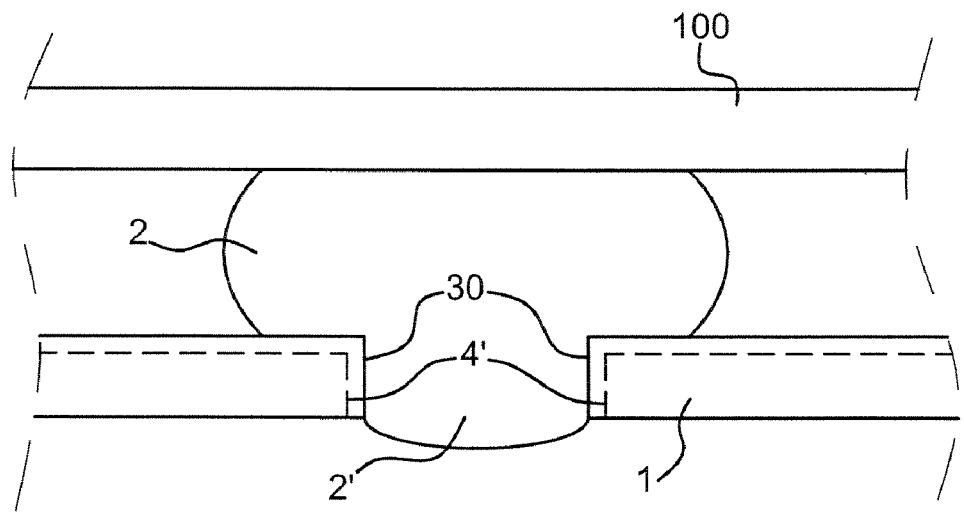
Figure 8:
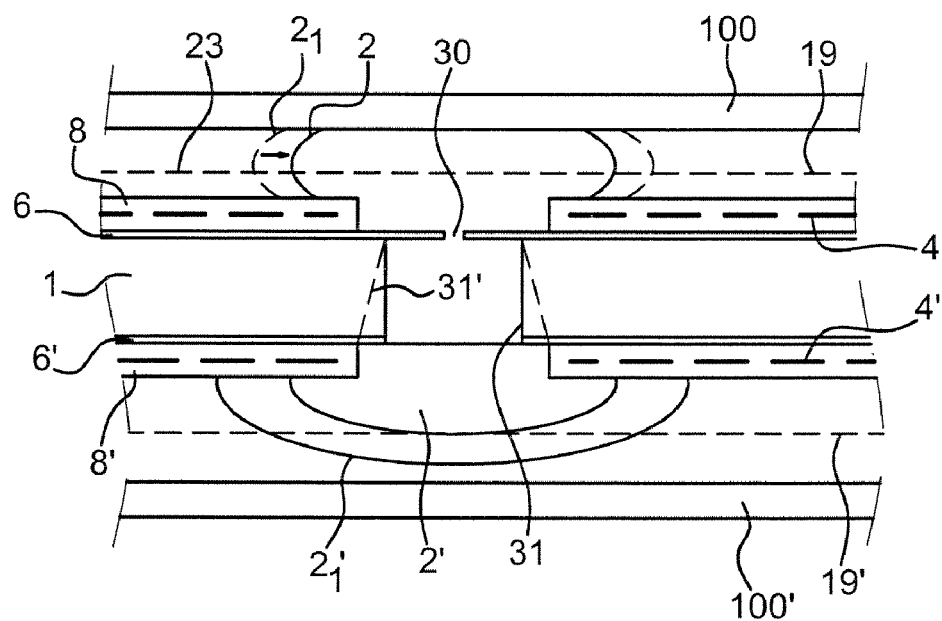
Figure 9:
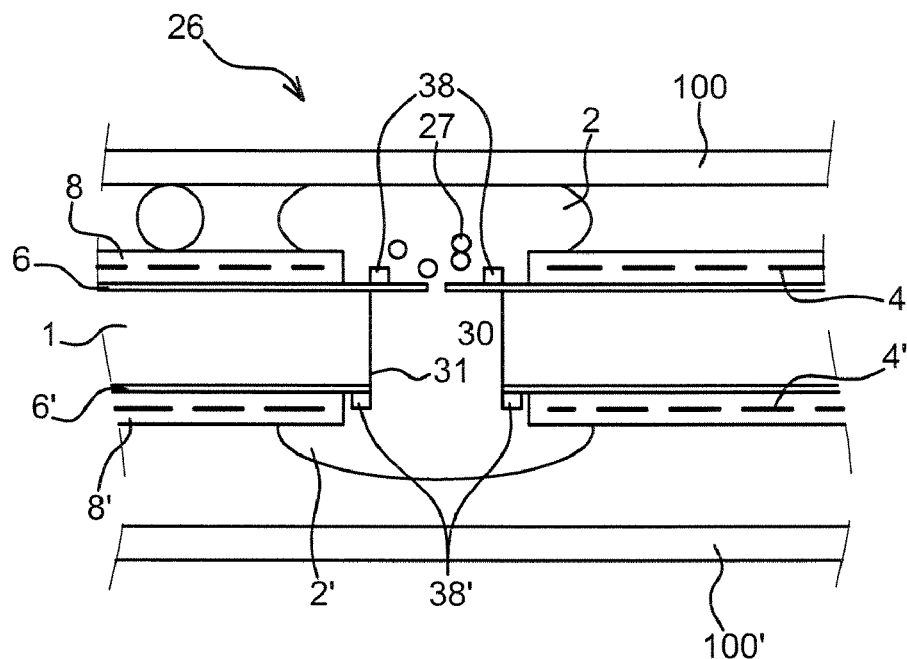
Figure 10:
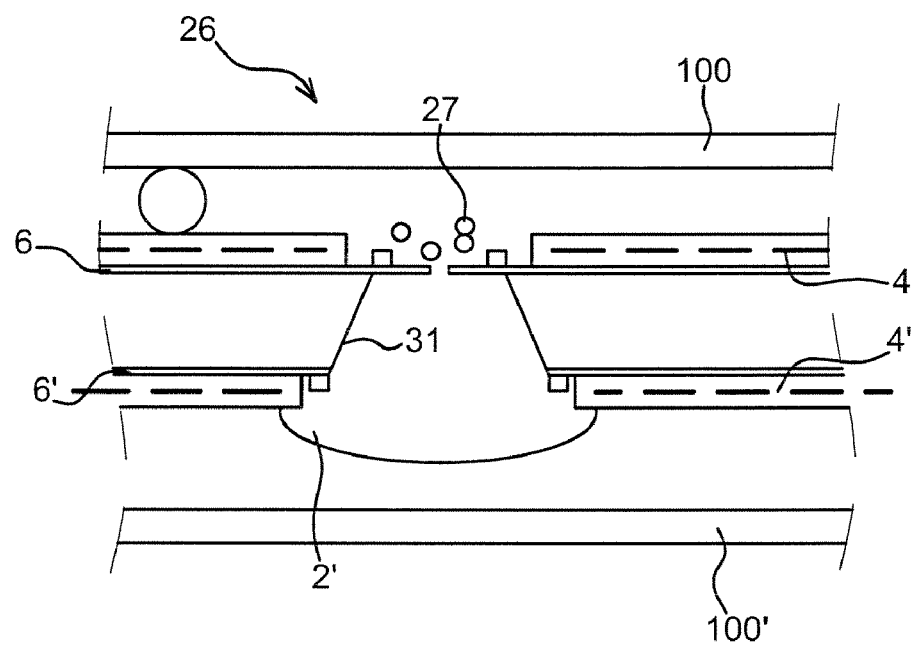
Figure 11:
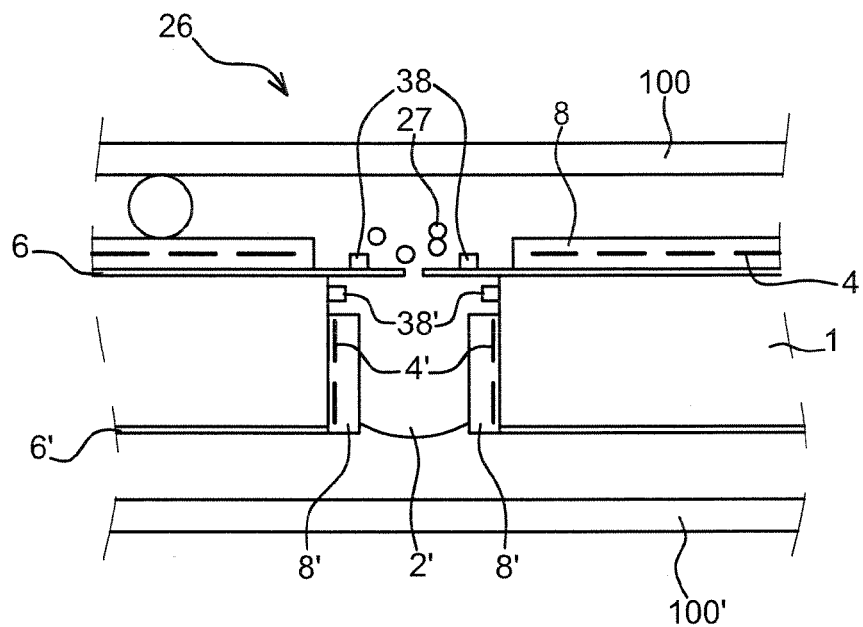
Figure 12:
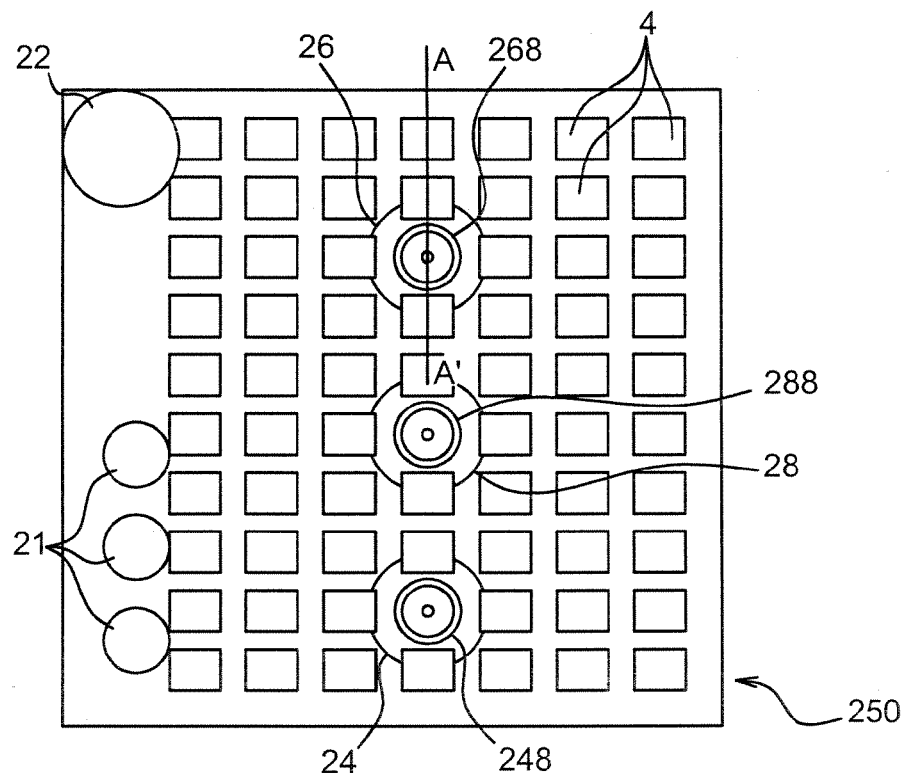

FIGS. 1A-1C illustrate the principle for displacing drops by electrowetting, FIG. 2 illustrates a closed configuration of a device for displacing drops, FIGS. 3A and 3B illustrate a mixed configuration of a device for displacing drops, FIGS. 4 and 5A-5B illustrate a device for displacing drops, wherein the upper cap is provided with an electrode, FIGS. 6A-7B illustrate various embodiments of a pumping device according to the invention, FIG. 8 illustrates a detailed view of another pumping device according to the invention, FIGS. 9-11 illustrate various embodiments of a measurement device of the <<patch clamp>> type according to the invention, FIG. 12 illustrates a top view of another device according to the invention, including several measurement sites, FIGS. 13A-13D illustrate a well or reservoir of liquid, FIG. 14 illustrates a device of the patch-clamp type according to the prior art.

DETAILED DISCUSSION OF PARTICULAR EMBODIMENTS

A pumping device according to the invention applies a device for displacing or handling drops of liquid by electrowetting, as described below in connection with FIGS. 6A-7B. These drops 2, 2' are in contact with a first and a second face 11, 11' of a substrate 1, provided with an aperture or an orifice 30.

The obtained pumping device is therefore compact and customized for each measurement site, allowing the pumping of small volumes of liquid in a pumping site and not requiring means such as fluid suction conduits.

Such a device may further allow formation and forwarding of the drops 2, 2' of liquid towards a pumping site.

In a pumping method and device according to the invention, one of the drops is caused to have a larger volume by electrowetting.

With electrowetting, it is possible to change the wetting angle and the radius of curvature of this drop or of both drops.

With electrowetting, it is also possible to change the electrostatic pressures in the drops. Indeed, if by electrowetting, the wetting angle of one of the drops is reduced on the surface on which it lies, the radius of curvature of the interface between this drop and its external environment will increase, causing a reduction in pressure inside it.

Vice versa, if the wetting angle of one of the drops with the surface with which it is in contact is increased, the radius of curvature of the interface between this drop and its external environment will decrease, causing an increase in pressure inside it. The drop retracts and pressure increases therein, because of the increase in the radius of curvature.

A first embodiment of a device for displacing and handling drops of the open system type and which may be applied within the scope of the invention, is illustrated in FIGS. 1A-1C.

This embodiment applies a device for displacing or handling drops of liquid based on the principle of electrowetting on a dielectric.

Examples of such devices are described in the article by M. G. Pollack, A. D. Shendorov, R. B. Fair, entitled <<Electrowetting-based actuation of droplets for integrated microfluidics>>, Lab on Chip 2 (1) (2002) 96-101.

The forces used for displacing drops of liquid are then electrostatic forces.

Document FR 2 841 063 describes a device further applying a catenary facing the activated electrodes for the displacement.

The principle of this type of displacement is summarized in FIGS. 1A-1C.

A drop 2 lies on a network 4 of electrodes, from which it is insulated by a dielectric layer 6 and a hydrophobic layer 8 (FIG. 1A).

The hydrophobicity of this layer means that the drop has a contact or wetting angle on this layer larger than 90°.

The electrodes 4 are themselves formed at the surface of a substrate 1.

When the electrode 4-1 located in proximity to the drop 2 is activated by switching means 14, the closing of which establishes a contact between this electrode and a voltage source 13 via a common conductor 16, the dielectric layer 6 and the hydrophobic layer 8 between this activated electrode and the drop under voltage act as a capacitor.

The counter-electrode 10 allows a possible displacement by electrowetting at the surface of the hydrophobic surface; it maintains an electric contact with the drop during such a displacement. This counter-electrode may either be a catenary as in FR-2 841 063, or a buried wire or a planar electrode in the cap of a confined system (such a confined system is described later on).

In an open system, if there is no displacement, it is possible to spread the drop on the hydrophobic surface without any counter-electrode. For example, this is the case if the drop may be brought onto the hydrophobic surface by a conventional dispensing system, the electrodes 4-1, 4-2 only being used for spreading or deforming the drop at the location where it was deposited.

The drop may thus be possibly displaced step by step (FIG. 1C) on the hydrophobic surface 8, by successive activation of the electrodes 4-1, 4-2, . . . etc, along the catenary 10.

It is therefore possible to displace liquids, but also to mix them (by approaching them with drops of different liquids), and to produce complex protocols.

The aforementioned documents give exemplary embodiments of series of adjacent electrodes for handling a drop in a plane, the electrodes may actually be positioned linearly, but also in two dimensions, thereby defining a plane for displacing the drops.

FIG. 2 illustrates another embodiment of a device for displacing or handling drops of the closed or confined system type, which may be applied within the scope of the invention.

In this figure, numerical references identical with those of FIGS. 1A-1C designate the same components therein.

This device further includes an upper substrate 100, preferably also covered with a hydrophobic layer 108. This assembly may possibly be transparent, allowing observation from the top.

FIGS. 3A and 3B, in which numerical references identical with those of FIG. 2 designate identical or similar components therein, illustrate a mixed displacement or handling system for drops, in which a drop 2 is initially in an open medium (FIG. 3A), activation of electrodes 4-1, 4-2, 4-3 allow the drop to be flattened (FIG. 3B) in a closed system, in an area where the system is provided with a cap, as illustrated above in connection with FIG. 2.

FIG. 4 illustrates an alternative of the closed system with a conducting cap 100, including an electrode or a network of electrodes 112, as well as an insulating layer 106 and a hydrophobic layer 108.

The catenary 10 of the preceding figures is replaced with the electrode 112 in this embodiment. Activation of this electrode 112 and of the electrodes 4 allows the drop to be displaced into the intended position and then to be stretched and deformed, in order to bring it onto the path of a light beam 50.

FIGS. 5A and 5B, in which numerical references identical with those of FIG. 4 designate identical or similar components therein, illustrate a mixed system, in which a drop 2 is initially in an open medium (FIG. 5A), activation of electrodes 4-1, 4-2, 4-3 allows the drop to be flattened (FIG. 5B) in a closed system, in an area where the system is provided with a cap, as illustrated above in connection with FIG. 4.

A device according to the invention may further include means which will allow the electrodes 4 to be controlled or activated, for example a PC type computer and a system of relays connected to the device or to the chip, such as the relays 14 of FIG. 1A, these relays being controlled by PC type means.

Typically, the distance between a possible conductor 10 (FIGS. 1A-5B) on the one hand and the hydrophobic surface 8 on the other hand is for example comprised between 1 μm and 100 μm or 500 μm.

This conductor 10 may for example appear as a wire with a diameter between 10 μm and a few hundreds of μm, for example 200 μm. This wire may be a gold or aluminium or tungsten wire or of other conducting materials.

When both substrates 1, 100 are used (FIGS. 2-5B), they are separated by a distance, for example between 10 μm and 100 μm or 500 μm.

Regardless of the relevant embodiments, a drop of liquid 2 may have a volume between for example 1 picoliter and a few microliters, for example between 1 μl and 5 μl or 10 μl.

Further, each of electrodes 4 will for example have a surface of the order of a few tens of $\mu m^2$ (for example 10 $\mu m^2$) right up to 1 $mm^2$, depending on the size of the drops to be transported, the spacing between neighboring electrodes being for example between 1 μm and 10 μm.

Structuration of the electrodes 4 may be obtained by standard methods of microtechnologies, for example by photolithography.

Methods for making chips incorporating a device according to the invention may be directly derived from the methods described in document FR-2 841 063.

Conductors, and notably conductors 110, may be made by depositing a conductive layer and etching this layer according to the suitable pattern of conductors, before depositing the hydrophobic layer 108.

The electrodes may be made by depositing a metal layer (for example in a metal selected from Au, Al, ITO, Pt, Cr, Ti, Cu) by photolithography. The substrate is then covered with a dielectric layer, for example in $Si_3N_4$ or $SiO_2$. Finally, deposition of a hydrophobic layer is carried out, such as for example a Teflon coating produced by a turntable.

Such a device for displacing drops may apply a two-dimensional network of electrodes which will allow liquids to be displaced step by step in or on a plane, to be mixed in order to achieve complex protocols.

In the case of the embodiment with catenaries 10 (FIGS. 1A-3B), a two-dimensional (2D) set of these catenaries may be made above the 2D set of electrodes 4. In the case of the embodiment with a counter-electrode 112 incorporated into the cap 100 (FIGS. 4-5B), this counter-electrode may also have a two-dimensional structure.

An example of such a two-dimensional network will be described below in connection with FIG. 12.

A pumping device according to the invention includes an electrowetting device, as illustrated in FIGS. 6A (top view) and 6B (side view).

Such a device includes a structure such as one of those described above in connection with FIGS. 1A-5B. The illustrated structure on the FIGS. 6A and 6B is of the closed configuration type, with a substrate 1, in which electrowetting electrodes 4 are positioned, and a cap 100, which is not illustrated in detail but which is for example similar to the cap of FIG. 4 (with a hydrophobic surface 108 and a buried electrode 112).

In this embodiment, like in the following ones, the substrate 1 may also include two substrates placed back to back, each of them may further have a structure for example according to one of FIGS. 1A-5B, and include electrowetting electrodes.

With the electrodes 4, it will be possible with the counter-electrode of the substrate 100 to control the displacement of a drop 2 localized between both substrates 1, 100.

A second drop 2' may be positioned by capillarity against the face 11' of the substrate 1 opposite to the face 11 with which the drop 2 is in contact.

An orifice 30 provides communication between both sides of the substrate 1.

The pumping principle according to the invention is then the following.

The change in the potentials of the electrodes 4, in the vicinity of a drop 2 will change the electrostatic pressure in this drop; if the wetting angle of this drop is reduced, the radius of curvature of its interface with its environment will increase, causing a decrease in the pressure inside it.

If the electric potential of the electrodes 4 is reduced, the drop 2 retracts and the pressure inside it will increase, because of the reduction of the radius of curvature.

The variations of pressure in the drop 2 will be reflected in the drop 2', the liquid of which will thereby be able to be pumped or discharged through the orifice 30.

A pressure variation between both volumes of liquid 2, 2', located in contact through the orifice 30 of the substrate may therefore be achieved by electrowetting.

According to an illustrated alternative in FIG. 7A, electrowetting electrodes 4, 4' are present on both sides of the substrate 1, with which both pressure in the drop 2 and that in the drop 2' may be controlled.

Thus, both drops 2, 2' will be able to be displaced and/or deformed on either side of the substrate 1.

Both series of electrodes may be made with one of the methods already described above. They may be driven by control means as already described above.

The same mechanism as described above then applies to the drop 2' and to the electrodes 4': if the wetting angle of this drop is reduced, the radius of curvature of its interface with its environment will increase, causing a decrease in the pressure inside it; if the electric potential of the electrodes 4' is reduced, the drop 2' retracts and the pressure inside it will increase, because of the decrease of the radius of curvature.

The illustrated configuration is closed on one of the sides and is open below (a wire or a catenary as in FIGS. 1A-1C may be used for the lower non-confined portion, of FIGS. 6B, 7A). But it is possible to achieve a doubly closed or confined or mixed configuration, with two caps 100, 100' on either side of the substrates 1. It would also be possible to have an open configuration in the upper portion (on the side of the drop 2) as in the lower portion, with possible catenaries on each side.

According to still another alternative, illustrated in FIG. 7B, the electrowetting electrodes 4' present on one of the surfaces of the substrate 1, and with which the pressure in the drop 2' may be controlled, are located in the wall of the orifice 30. With this configuration, it is possible to have a small radius in the lower chamber in an open system.

The same mechanism as described above then applies to the drop 2' and to the electrodes 4': if the wetting angle of this drop is reduced, the radius of curvature of its interface with its environment will increase, causing reduction in the pressure inside it; if the electric potential of the electrodes 4' is reduced, the drop 2' retracts and the pressure inside it will increase, because of the decrease of the radius of curvature.

Regardless of the contemplated embodiment of a pumping device according to the invention, a physical relationship exists between the pressures in the drops 2, 2' and their wetting angles.

The pressure in the confined drop 2 is given by Laplace's law.

$$P_1 = \gamma \left( \frac{1}{R_1} + \frac{1}{R_2} \right) \quad (1)$$

where $R_1$ and $R_2$ are the two radii of curvature in the vertical and horizontal planes, or parallel and perpendicular to the plane defined by the substrate 1.

The radius $R_1$ is directly related to the volume $V_1$ of drop 2 by:

$$R_1 = \left( \frac{V_1}{\pi \delta} \right)^{\frac{1}{2}} \quad (2)$$

where $\delta$ is the distance between the plates 1, 100.
On the other hand, it may be shown that:

$$R_2 = \frac{\delta}{-2\cos\theta_0} \quad (3)$$

where $\theta_0$ is the contact angle with the plates. The pressure in the drop is then:

$$P_1 = \gamma \left( \left( \frac{\pi \delta}{V_1} \right)^{\frac{1}{2}} + \frac{-2\cos\theta_0}{\delta} \right) \quad (4)$$

In order to increase the pressure in the confined drop 2, it is sought to make $R_2$ small.

According to an exemplary numerical application, by assuming $\theta_0=120°$, $\delta=50$ μm, $\gamma=40$ mN/m and $V_1=1$ μl, a pressure $P_1=816$ Pa is found.

The pressure in the drop 2' is also given by Laplace's law:

$$P_2 = \frac{2\gamma}{R_3} \quad (5)$$

In the open configuration, the pressure in the drop 2' is given by Laplace's law. One then has:

$$P_1 = \frac{2\gamma}{R_1} \quad (5')$$

like equation (5).

The radius of curvature $R_3$ is related to the volume $V_2$ of the drop and to the contact angle $\theta_2$ by:

$$V_2 = \frac{\pi}{3} R_3^3 (2 - 3\cos\theta_2 + \cos^3\theta_2) \quad (6)$$

The pressure in the drop 2' is then:

$$P_2 = \frac{2\gamma}{\left(\frac{3V_2}{\pi(2 - 3\cos\theta_2 + \cos^3\theta_2)}\right)^{\frac{1}{3}}} \quad (7)$$

According to an exemplary numerical application assuming $\theta_2=80°$, $\gamma=40$ mN/m and $V_2=100$ μl, a pressure in the drop $2'$ equal to $P_2=$Pa is obtained. The value of the surface tension $\gamma=40$ mN/m corresponds to the case of a liquid with surfactants. More generally, this value is between 10 and 75 mN/m (for example: 10 if this is oil with surfactants in the drop).

The pressure difference obtained by the system is therefore:

$$\Delta P \cong \gamma\left(\left(\frac{\pi\delta}{V_1}\right)^{\frac{1}{2}} + \frac{-2\cos\theta_0}{\delta}\right) - \frac{2\gamma}{\left(\frac{3V_2}{\pi(2 - 3\cos\theta_2 + \cos^3\theta_2)}\right)^{\frac{1}{3}}} \quad (8)$$

With the numerical values considered earlier, $\Delta P=796$ Pa is obtained.

As both volumes of liquid 2, 2' are in communication, the pressure difference then re-equilibrates, but it is maintained for a sufficient time to allow a pumping effect.

Another embodiment of a pumping device according to the invention is illustrated in FIG. 8.

In this figure, the substrate 1 is in a semiconducting material such as silicon. On one of its faces, a dielectric coat 6 (for example, in $Si_3N_4$ or $SiO_2$) is pierced with a hole 30 with a diameter between 1 and 2 μm, for example and, on the face opposite to it, with a hole with a width or maximum dimension between 50 and 1,000 μm for example.

This dielectric is then coated with a network of electrodes 4; these electrodes are then passivated, i.e. electrically insulated, for example by a new layer of dielectric on which a hydrophobic coating 8 is produced, for example of the Teflon type.

The other face of the substrate 1 is treated in the same way, with an insulator 6', electrodes 4' and a hydrophobic layer 8'.

With oil 23, it is possible to prevent or limit or avoid evaporation of the drops.

The drops 2 in the upper portion are, in the illustrated embodiment, confined, because of the contact with the preferentially transparent substrates 1, 100, and the <<wet>> surface of which is made hydrophobic for example by a Teflon type coating. The substrates 100, 100' are substantially similar to the substrate 100 described above, for example in connection with FIG. 2.

In fact, two positions of each of the drops are illustrated in this FIG. 8: position 21 of the drop 2 before compression, and a position $2'_1$ of the drop 2' after expansion of the latter following compression of the drop 2.

This contact with a cap 100, 100' with a hydrophobic surface and including conducting means allows the potential of the drop 2, 2' to be controlled.

Alternatively, this control may also be achieved by means of a catenary 19 and/or 19' (illustrated in dashed lines in FIG. 8) crossing through the drop as shown above in connection with FIGS. 1A-1C, therefore in an open configuration. This configuration is also possible for the pumping with a catenary. This contact does not change, or only very little, the pressures in the drops.

In the illustrated example, the orifice 30 is not of a maximum diameter or dimension, as measured in the plane of the substrate 1, uniform along the direction perpendicular to this substrate. A second portion 31 has a wider diameter.

An application of a pumping device according to the invention to an electric measurement device of the <<patch-clamp>> type will now be described.

Such a device is illustrated in FIG. 9.

It includes a pumping structure similar to the one described above, for example in connection with FIG. 8.

It further includes electrodes 38, 38' with which it will be possible to achieve measurement of the variation of an electric characteristic of the liquid medium when a cell 27 is attracted against the hole 30 and pressed or invaginated against or in this hole (as cell 327' in FIG. 14). In particular, it is of interest to then conduct a measurement of resistance or resistivity of the medium. Typically, the presence of a cell 27 in the hole 30 results in a change of resistance of the order of several MΩ. If there is a preferential contact at the dielectric/cell interface, the resistance reaches values between 50 MΩ and 10 GΩ.

As already indicated above, the electrodes 4 which are used for electrowetting, as well as the electrodes 38 used for the electrophysiological measurement, are on a dielectric membrane 6, the coating 8 of which is hydrophobic and passivated in the displacement areas of the drops.

On the other hand, in the measurement areas in which electrodes 38, 38' are positioned, the coating 6, 6' is hydrophilic and non-passivated. Ag/AgCl electrodes are quite suitable for locally changing the concentrations of chlorine ions and activating the potassium channels of cells.

The measurement electrodes 38, 38' will allow a potential difference to be applied and the current to be measured in the liquid medium present in the cavity. With conductors, not shown in the figure, it is possible to apply the intended voltage between both electrodes. This voltage is for example driven or controlled by means which provide control or activation of the electrodes 4, for example a PC type computer having suitable interfaces. With these conductors, it will also be possible to measure the current variation between the electrodes 38, 38' when a cell is brought onto the measurement site. This variation may be stored in memory storage means of a device with which the data thereby sampled during the measurements may then be processed and analyzed, for example by converting them into a current measurement or any other electric characteristic. A current amplifier may also be combined with the device, in order to measure current variations during the positioning of the cell on the orifice 30.

In order to electrically insulate a membrane fragment of a cell, the cells 27—for example in a drop 2—may be brought to a measurement site 26 by electrowetting, such as the one illustrated in FIG. 9. While the cells settle, a depression may be generated in the way as already described above, by the pumping method according to the invention, between the lower and upper chambers or between the drops 2 and 2'. A cell is then attracted onto the hole 30 of the dielectric membrane 6. Finally a single cell is therefore studied. Once the membrane of the cell is on the hole 30, the latter deforms and then invaginates into the hole. The electric resistance measured at the cell/dielectric contact 6 may then be of the order of one giga-ohm. With this resistance, it is possible to view for example on an amplifier dedicated to electrophysiology, currents of the order of one pico-ampere. These currents for example result from the passing of the ions through channel proteins of the cell membrane.

Forming the apertures 30, 31 in the substrate of FIGS. 6A-10 may be achieved by different etching methods.

If this substrate is in silicon, anisotropic etching will preferentially be used. This etching by KOH or TMAH has the advantage of being performed at low temperature (<90° C.) and does not require re-treatment of the surfaces. Indeed, deep etching of silicon applies a sequential process which alternates etching and passivation steps by using fluorinated polymers known for their hydrophobicity. The re-treatments may be chemical or thermal but this latter alternative should be avoided when using metals. For this reason, it is preferable to form an aperture 31 by wet etching or by wet chemistry. This embodiment is illustrated in FIG. 10. In this case, the aperture 31 is in the shape of a truncated pyramid. Such an aperture may also be made in a pumping device as described above in connection with FIGS. 6A-8 (see for example the aperture 31' illustrated in dashed lines in FIG. 8).

FIG. 11 describes a configuration in which the electrodes 4', which allow the depression to be created, would no longer be located on a face of the substrate 1 parallel to a main plane of this substrate, but in the walls of the orifice 31. The pumping principle remains the same, as explained above in connection with FIG. 7B. The coating 8' is also applied to the walls of the orifice 30, the electrodes 4' being passivated, whereas the electrodes 38' remain depassivated. A potential difference which allows a measurement is applied between the electrodes 38, 38'. Pumping occurs as explained above in connection with FIGS. 7A and 7B.

The drops 2, 2' may be brought to a measurement site 26 by displacement by electrowetting, with electrodes 4, 4', as explained above in connection with FIGS. 1A-1C in an open configuration, or also in a closed configuration (FIGS. 2-5C). They may also be brought or positioned manually, by means of a pipette.

A device according to the invention may be incorporated into a network of measurement sites.

Thus, another embodiment of the invention is illustrated in a top view in FIG. 12, without the caps 100, 100'.

This device first includes a two-dimensional device for displacing and handling drops by electrowetting, for example of the type as discussed above in connection with FIGS. 1A-5C, and for which only the electrodes 4 of the substrate 1 are illustrated schematically.

References 22 and 21 designate several reservoirs, for example a reservoir 22 of cells and one or more drug reservoirs 21. In certain cases, a single reservoir may be sufficient. It is also possible not to use any reservoir and to bring the volumes of liquid to be analyzed by other means, for example a pipette.

The system may further include a site 26 for a single measurement, as described above in connection with FIGS. 9-11, or at least such a site. For example, this device may include a plurality of such sites 24, 26, 28, each identical or similar to the one described above in connection with FIGS. 9-11. References 268, 248, 288 designate measurement electrodes equivalent to the electrode 38 of FIGS. 9-10.

The reservoirs 21, 22 are advantageously compatible with a format of well plates (8, 96, 384, 1586 wells).

An exemplary embodiment of these reservoirs 21 or 22 will be given below in connection with FIGS. 13A-13D.

Figure 13A:
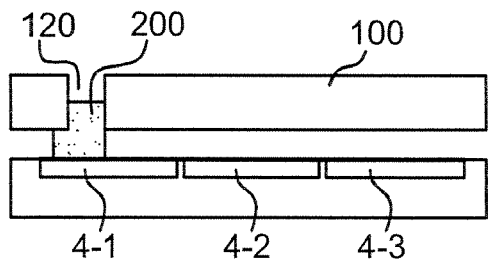
Figure 13B:
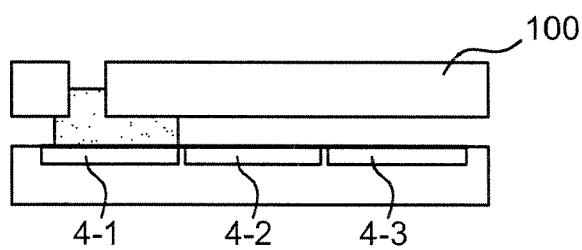
Figure 13C:
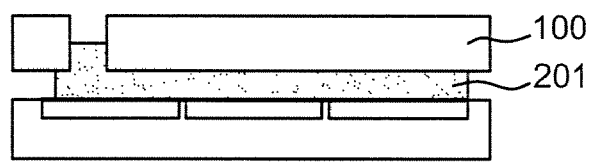
Figure 13D:
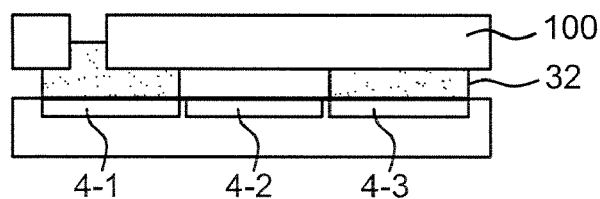

A liquid 200 to be dispensed is deposited in a well 120 of this device (FIG. 13A). This well is for example made in the upper cap 100 of the device. The lower portion, illustrated schematically in FIGS. 13A-13D, is for example similar to the structure of FIGS. 1A-1C.

Three electrodes 4-1, 4-2, 4-3, similar to the electrodes 4 for displacing drops of liquid, are illustrated in FIGS. 11A-11D.

The activation of these series of electrodes 4-1, 4-2, 4-3 leads to spreading of a drop from the well 120, and therefore to a liquid segment 201 as illustrated in FIG. 11C.

Next, this liquid segment is cut by disabling one of the enabled electrodes (electrode 4-2 in FIG. 11C). A drop 2 is thereby obtained, as illustrated in FIG. 11D.

A series of electrodes 4-1, 4-2, 4-3 is therefore used for stretching the liquid from the reservoir 120 into a finger 201 (FIGS. 11B and 11C) and for cutting this finger 201 of liquid (FIG. 11D) and forming a drop 2 which will be able to be carried away to any measurement site as described above.

This method may be applied by inserting electrodes such as the electrodes 4-1 between the reservoir 120 and one or more electrodes 4-2, a so-called cutting electrode.

If a configuration with another cap is not used, the microdrops may be dispensed with a pipette or an automatic dispensing device.

A device according to the invention may be used for immobilizing biological objects other than cells for which the intention is to study electrophysiological activity. For example, the invention may be applied to bovine ovocytes for in vitro fertilization or even to the displacement of embryos. The biological objects may then be flattened by suction.

With a device according to the invention it is possible to displace volumes of fluid as drops. The drops may integrate solids or biological elements of large sizes such as embryos (sizes between 0.3 mm and 1 mm). With the present invention, it is possible to displace and to locally block such an object by suction means. This system may be used as already mentioned above for handling embryos or for in vitro fertilization (IVF) of ovocytes.

The invention claimed is:

1. An apparatus comprising:
   a substrate, having a first and a second surface, at least one of which is hydrophobic or covered with a hydrophobic layer, and at least one orifice crossing through said substrates;
   means for displacing, by electrowetting, a volume of liquid on one of said faces of the substrate through said orifice; and
   first and second electrodes configured to be in direct contact with the volume of liquid as the volume of liquid is displaced through said orifice, to be controlled by a computer, and to supply said computer with data regarding a variation of an electric characteristic of the volume of liquid as the volume of liquid is displaced through said orifice.

2. The apparatus according to claim 1, wherein the second surface of the substrate is hydrophobic or includes the hydrophobic layer, and the apparatus includes a plurality of electrodes, other than the first and second electrodes, disposed under said hydrophobic layer or surface.

3. The apparatus according to claim 1, wherein the first and second surfaces of the substrate are parallel to each other.

4. The apparatus according to claim 1, wherein the first surface of the substrate is parallel to a plane defined by the substrate, and the second surface is defined by at least one portion of a wall of said orifice.

5. The apparatus according to claim 1, wherein the electric characteristic is resistance or resistivity.

6. The apparatus of claim 1, further comprising the computer.

7. The apparatus of claim 1, wherein at least one of the first and the second electrodes is disposed at an edge of the orifice.

8. The apparatus of claim 1, wherein the first and the second electrodes are outside of the substrate and on the first and second surfaces of the substrate.

9. The apparatus according to claim 1, wherein said orifice includes a first portion, with a first maximum dimension, and a second portion, having a second maximum dimension, larger than the first.

10. The apparatus according to claim 1 or 9, wherein the means for displacing includes a plurality of electrodes disposed under said hydrophobic layer or surface.

11. The apparatus according to claim 1, further comprising a first dielectric layer, in part under the hydrophobic layer or surface.

12. The apparatus according to claim 11, further comprising a second dielectric layer, disposed on a surface parallel to the first surface.

13. The apparatus according to claim 1, further comprising at least one reservoir of liquid and means for bringing drops of liquid from the at least one reservoir towards the at least one orifice.

14. The apparatus according to claim 13, wherein the means for bringing the drops of liquid towards the at least one orifice includes another plurality of electrodes, other than the first and second electrodes.

15. The apparatus according to claim 1, further including a second substrate disposed to face at the first or the second surfaces.

16. The apparatus according to claim 15, wherein the second substrate includes a hydrophobic surface layer.

17. The apparatus according to claim 15 or 16, wherein the second substrate includes an electrode.

* * * * *